(12) United States Patent
Vannuffelen et al.

(10) Patent No.: US 7,336,356 B2
(45) Date of Patent: Feb. 26, 2008

(54) METHOD AND APPARATUS FOR DOWNHOLE SPECTRAL ANALYSIS OF FLUIDS

(75) Inventors: Stephane Vannuffelen, Tokyo (JP); Kentaro Indo, Machida (JP); Go Fujisawa, Sagamihara (JP); Toru Terabayashi, Sagamihara (JP); Tsutomu Yamate, Yokohama (JP)

(73) Assignee: Schlumberger Technology Corporation, Sugar Land, TX (US)

( * ) Notice: Subject to any disclaimer, the term of this patent is extended or adjusted under 35 U.S.C. 154(b) by 98 days.

(21) Appl. No.: 11/307,170

(22) Filed: Jan. 26, 2006

(65) Prior Publication Data

US 2007/0171412 A1    Jul. 26, 2007

(51) Int. Cl.
*G01J 3/28* (2006.01)
*G01N 21/00* (2006.01)
*G01V 5/08* (2006.01)

(52) U.S. Cl. .................... 356/326; 356/436; 250/269.1
(58) Field of Classification Search ..................... None
See application file for complete search history.

(56) References Cited

U.S. PATENT DOCUMENTS

| | | | |
|---|---|---|---|
| 3,780,575 A | 12/1973 | Urbanosky | |
| 3,859,851 A | 1/1975 | Urbanosky | |
| 4,860,581 A | 8/1989 | Zimmerman et al. | |
| 4,994,671 A | 2/1991 | Safinya | |
| 5,167,149 A | 12/1992 | Mullins et al. | |
| 5,201,220 A | 4/1993 | Mullins et al. | |
| 5,331,156 A | 7/1994 | Hines et al. | |
| 6,437,326 B1 * | 8/2002 | Yamate et al. | 250/269.1 |
| 6,476,384 B1 | 11/2002 | Mullins et al. | |
| 7,196,786 B2 * | 3/2007 | DiFoggio | 356/301 |
| 2002/0185604 A1 | 12/2002 | Coates et al. | |
| 2004/0019462 A1 | 1/2004 | Gehrlein et al. | |

FOREIGN PATENT DOCUMENTS

EP    1 574 838 A1    9/2005

* cited by examiner

*Primary Examiner*—Gregory J. Toatley, Jr.
*Assistant Examiner*—Gordon J. Stock, Jr.
(74) *Attorney, Agent, or Firm*—Karan Singh; Jaime Castano; Dale Gaudier

(57) ABSTRACT

A downhole fluid analysis system comprises an input light signal that is directed through a fluid sample housed in a sample cell. The input light signal may originate from a plurality of light sources. A light signal output from the sample cell is then routed to two or more spectrometers for measurement of the represented wavelengths in the output light signal. The output of the spectrometers is then compared to known values for hydrocarbons typically encountered downhole. This provides insight into the composition of the sample fluid. Additionally, the input light can be routed directly to the two or more spectrometers to be used in calibration of the system in the high temperature and noise environment downhole.

21 Claims, 7 Drawing Sheets

METHOD AND APPARATUS FOR DOWNHOLE SPECTRAL ANALYSIS OF FLUIDS

FIELD OF THE INVENTION

The present invention relates to methods and apparatus for fluid analysis using a spectrometer architecture downhole in subterranean formation evaluation and testing for the purpose of exploration and development of hydrocarbon-producing wells, such as oil or gas wells. More specifically, a fluid analysis module with at least two spectrometers is used in characterizing downhole fluid.

BACKGROUND OF THE INVENTION

In order to evaluate the nature of underground formations surrounding a borehole, it is often desirable to obtain and analyze samples of formation fluids from a plurality of specific locations in the borehole. Over the years, various tools and procedures have been developed to facilitate this formation fluid evaluation process. Examples of such tools can be found in U.S. Pat. No. 6,476,384 ("the '384 patent"), assigned to Schlumberger Technology Corporation ("Schlumberger"). The disclosure of this '384 patent is hereby incorporated by reference as though set forth at length.

Schlumberger's Repeat Formation Tester (RFT) and Modular Formation Dynamics Tester (MDT) tools are specific examples of sampling tools as described in the '384 patent. In particular, the MDT tool includes a fluid analysis module for analyzing fluids sampled by the tool.

Over the years, various fluid analysis modules have been developed for use in connection with sampling tools, such as the MDT tool, in order to identify and characterize the samples of formation fluids drawn by the sampling tool. For example, Schlumberger's U.S. Pat. No. 4,994,671 (also incorporated herein by reference) describes an exemplary fluid analysis module that includes a testing chamber, a light source, a spectral detector, a database, and a processor. Fluids drawn from the formation into the testing chamber by a fluid admitting assembly are analyzed by directing light at the fluids, detecting the spectrum of the transmitted and/or backscattered light, and processing the information (based on information in the database relating to different spectra) in order to characterize the formation fluids. Schlumberger's U.S. Pat. No. 5,167,149 and U.S. Pat. No. 5,201,220 (both of which are incorporated by reference herein) also describe reflecting light from a window/fluid flow interface at certain specific angles to determine the presence of gas in the fluid flow. In addition, as described in U.S. Pat. No. 5,331,156, by taking optical density (OD) measurements of the fluid stream at certain predetermined energies, oil and water fractions of a two-phase fluid stream may be quantified. As the techniques for measuring and characterizing formation fluids have become more advanced, the demand for more precise and expandable formation fluid analysis tools has increased.

Prior optical fluid analysis tools typically utilized a single light source directed at a sample cell and a single spectrometer to collect and analyze the light. In a typical embodiment, a filter array (FA) spectrometer is used which provides a maximum of about 20 channels. These tools are used downhole in adverse conditions which can affect the signal to noise ratio of the spectrometer.

The prior approaches while being largely effective also exhibit certain limitations. While the measurements from the single FA spectrometer are useful, it is desirable to have a system where multiple spectrometers of different types can be utilized downhole at the same time to analyze fluid. This would alleviate the need for multiple separate modules; a single light source may provide information to a group of different spectrometers increasing the number of channels available and the specificity of the overall system.

Adverse conditions downhole also make it necessary to calibrate a spectrometer system such as those in the prior art. This requires directing at least two beams of light, one reference signal and one measurement signal, at a spectrometer. This requires differentiation of light signals which can be achieved through the use of a light chopper, as disclosed in co-pending U.S. patent application Ser. No. 11/273,893 relating to real-time calibration for a downhole spectrometer. However, light choppers require a motor that increases the size of the downhole tool significantly.

SUMMARY OF THE INVENTION

In consequence of the background discussed above, and other factors that are known in the field of downhole fluid analysis, applicants recognized a need for an apparatus and method for broad spectral optical analysis while providing detailed spectral analysis in a range of interest. In this, applicants recognized that a spectral analysis system that is configured with a plurality of spectrometers, which are selected based upon the needs and requirements of the spectral analysis to be undertaken, would provide significant improvements in the accuracy and efficiency of downhole fluid analysis.

One embodiment of the invention comprises a method and apparatus for fluid analysis downhole using a spectrometer. In one aspect, one or more light sources are directed at a sample cell that contains fluid extracted downhole. The light transmitted through the sample is measured by two or more spectrometers for spectral analysis of the fluid. Additionally, light from the one or more light sources is routed directly to the same set of spectrometers to provide a reference measurement used in calibration. Two or more different types of spectrometers may be used, including, but not limited to, filter array and grating spectrometers.

Additional advantages and novel features of the invention will be set forth in the description which follows or may be learned by those skilled in the art through reading the materials herein or practicing the invention. The advantages of the invention may be achieved through the means recited in the attached claims.

BRIEF DESCRIPTION OF THE DRAWINGS

The accompanying drawings illustrate preferred embodiments of the present invention and are a part of the specification. Together with the following description, the drawings demonstrate and explain principles of the present invention.

Figure 1:
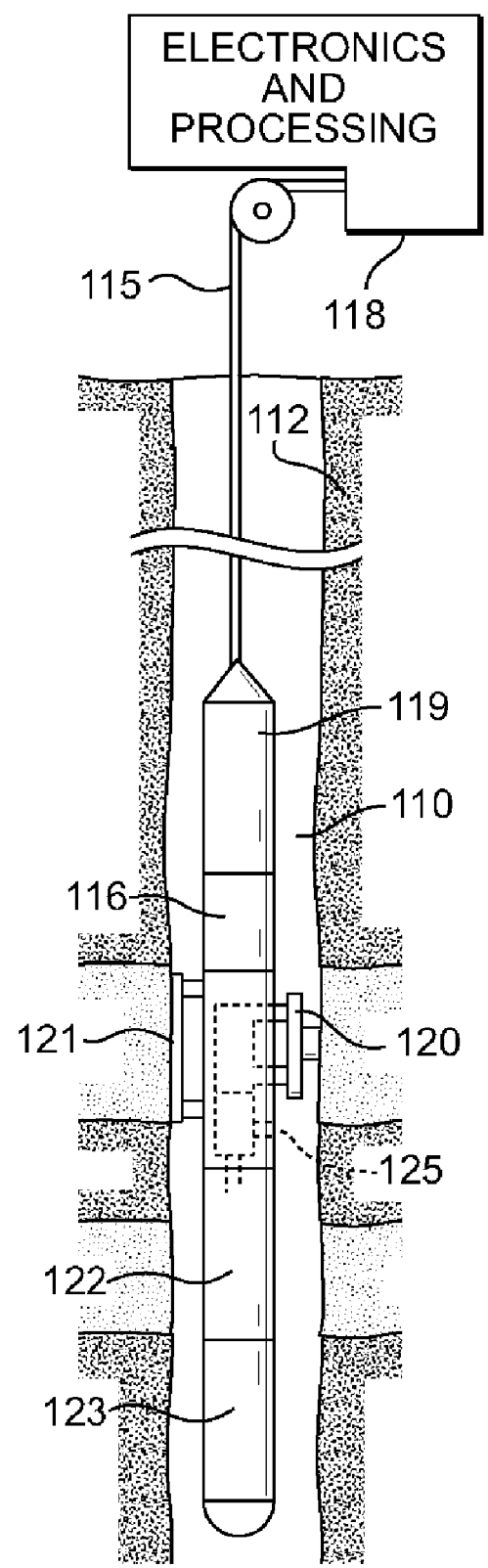
FIG. 1 is a schematic view of one exemplary context in which the present invention may be used.

Throughout the drawings, identical reference numbers indicate similar, but not necessarily identical elements. While the invention is susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the scope of the invention as defined by the appended claims.

DETAILED DESCRIPTION

Illustrative embodiments and aspects of the invention are described below. In the interest of clarity, not all features of an actual implementation are described in the specification. It will of course be appreciated that in the development of any such actual embodiment, numerous implementation-specific decisions must be made to achieve the developers' specific goals, such as compliance with system-related and business-related constraints, that will vary from one implementation to another. Moreover, it will be appreciated that such development effort might be complex and time-consuming, but would nevertheless be a routine undertaking for those of ordinary skill in the art having benefit of the disclosure herein.

FIG. 1 is a schematic diagram of an exemplary downhole tool 110 for testing earth formations and analyzing the composition of fluids from the formation. Downhole tool 110 is suspended in a borehole 112 from a cable 115 that is connected in a conventional fashion to a surface system 118. Surface system 118 incorporates appropriate electronics and processing systems for control of downhole tool 110 and analysis of signals received from the downhole tool.

Downhole tool 110 includes an elongated body 119, which encloses a downhole portion of a tool control system 116. Elongated body 119 also carries a selectively-extendible fluid admitting/withdrawal assembly 120 and a selectively-extendible anchoring member 121. Examples of the fluid admitting/withdrawal assembly are shown and described, for example, in Schlumberger's U.S. Pat. No. 3,780,575, U.S. Pat. No. 3,859,851, and U.S. Pat. No. 4,860,581. The disclosure of each of these patents is incorporated herein by reference. Fluid admitting/withdrawal assembly 120 and anchoring member 121 are respectively arranged on opposite sides of the elongated body 119. Fluid admitting/withdrawal assembly 120 is equipped for selectively sealing off or isolating portions of the wall of borehole 112, such that pressure or fluid communication with the adjacent earth formation can be selectively established. A fluid analysis module 125 is also included within elongated body 119 and formation fluid to be analyzed is channeled through the analysis module. The sampled fluid may then be expelled through a port (not shown) back into borehole 112, or sent to one or more sample chambers 122, 123 for recovery at the surface. Control of fluid admitting/withdrawal assembly 120, fluid analysis module 125, and the flow path to sample chambers 122, 123 is maintained by electrical control systems 116, 118.

Figure 2:
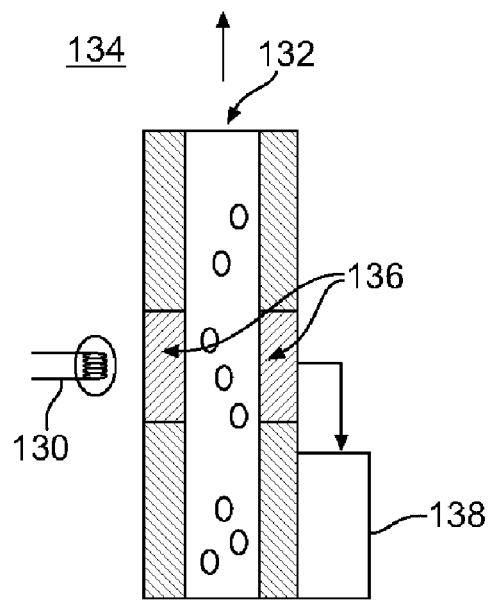
FIG. 2 is a schematic partial cross-sectional view of one exemplary structure of a fluid analysis module according to the present invention.

FIG. 2 shows one example of a spectral analysis module 134 that may be integrated into the tool 110. The formation fluid 132 is the sample of interest to the end user of the system. This fluid may contain any number of components including, but not limited to, gas, oil, and water. As mentioned above, it is highly desirable to know what fluids are present and in what relative quantities. To accomplish this, light source 130 is positioned to direct light toward one of the two optical windows 136. In one embodiment of the present invention, this light may be a halogen lamp, a light emitting diode (LED), a laser, or any other light source that can be introduced downhole. These light sources produce light across a wide spectral range, approximately 500-2000 nm in wavelength. The light produced by light source 130 is transmitted through the first optical window 136, through the sample fluid 132 and emerges from the second optical window 136. This light is collected and transmitted using fiber optic bundles which allows for the specific direction and routing of the light signals. The light of particular interest is that which is reflected, transmitted and/or emitted, i.e., the output light, from the sample fluid. This output light signal is directed (again, usually using fiber optics) to a spectrometer section 138 of the spectral analysis module. In prior systems, the spectrometer section typically contained a single FA spectrometer with a maximum of 20 channels. In one embodiment, the instant invention provides for a plurality of spectrometers to be included in the spectrometer section 138. This increases the number of available channels and also allows for a different type of spectrometer, such as a grating spectrometer, to be included in the detection and analysis of the output light signal. The output of the spectrometer section is used in determining the characteristics of the sample fluid 132.

Figure 3:
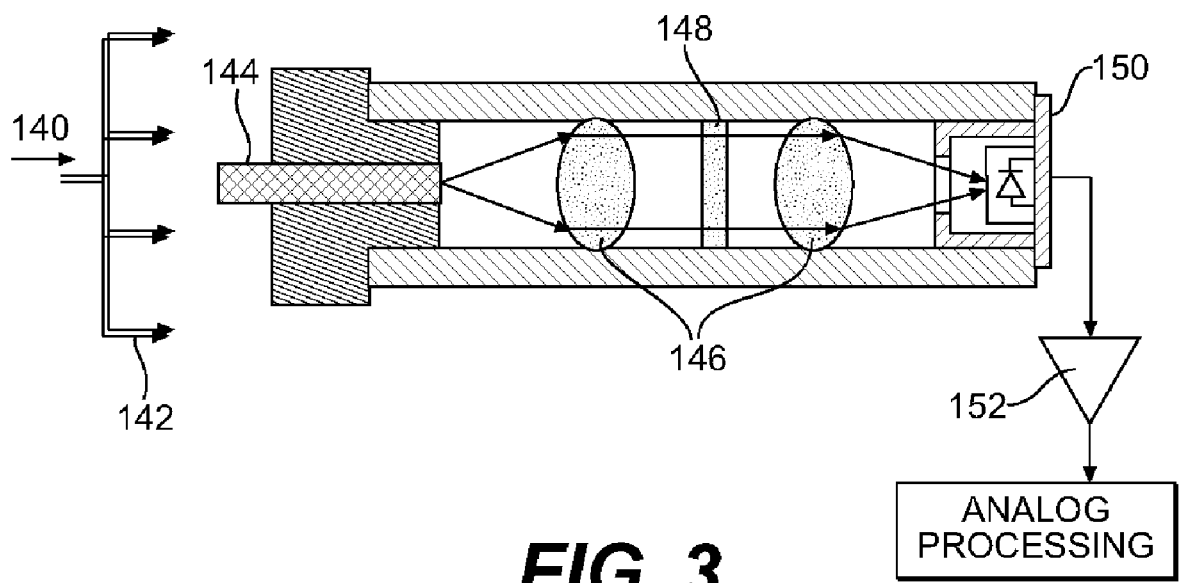
FIG. 3 is a cross-sectional schematic view of one filter channel in a larger filter array type spectrometer.

FIG. 3 is a schematic view of one of the channels of an FA spectrometer that is typically used in prior systems and may be used as one of the spectrometers in the instant invention. Light is input at 140 via a fiber optic bundle which allows the light to be routed to each of the channels through multiple paths labeled 142. One of those paths will deliver a light signal to input fiber bundle 144. This light then traverses through first lens 146 and through filter 148. Filter 148 is typically a bandpass filter. This bandpass filter will only allow light in a range of wavelengths to pass. The full spectrometer has a plurality of these filter elements, each of which may correspond to a different band of wavelengths. After moving through filter 148, the signal is refocused by the second lens 146 toward the output photodetector 150. This photodetector generates a current based on incident light with the current being proportional to the amount of incident light. This current is then converted to a voltage by I/V converter 152 and the voltage signal moves on for further processing. As can be seen, the voltage will differ for each tested wavelength and give an indication of the relative contributions of the different wavelengths. Based on control data, this will give insight to the composition of the sample fluid.

Figure 4:
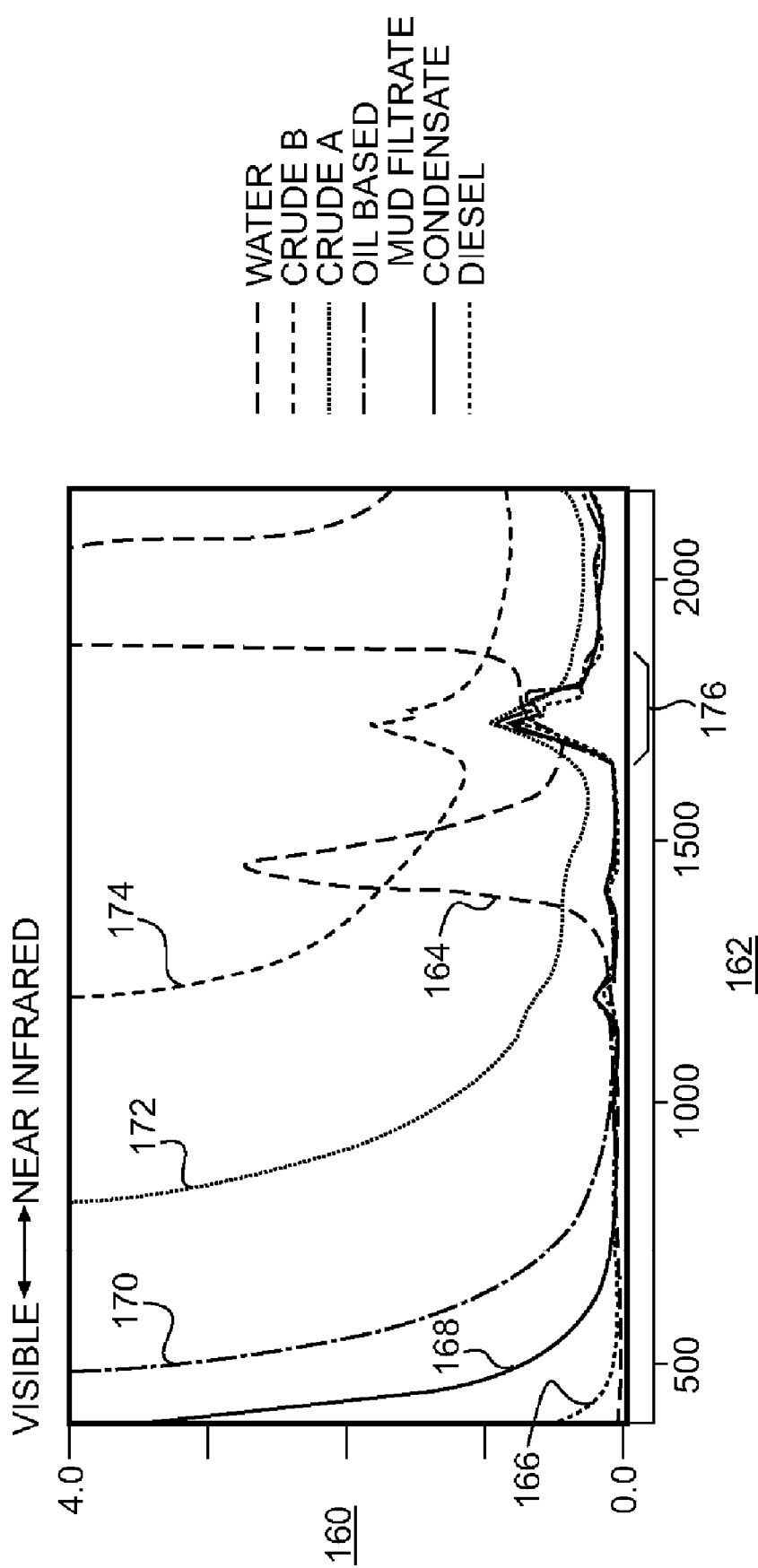
FIG. 4 is an illustrative representation of the absorption spectra of a number of hydrocarbons encountered downhole.

Optical absorption is wavelength dependent and is determined by the sample fluid composition. FIG. 4 shows the absorption characteristics of several hydrocarbons and other fluids that will likely be encountered downhole. Axis 162 is the wavelength of light transmitted and axis 160 is the corresponding optical density (OD). Water is shown by line 164, element 166 corresponds to diesel, element 168 corresponds to condensate, element 170 corresponds to oil based mud filtrate, element 172 corresponds to crude A, and element 174 corresponds to crude B. Several spectral regions can be discriminated and these regions give insight into the composition of the overall fluid. It is shown here that water peaks at about 1450 nm, just before a region of high interest where a number of hydrocarbons peak. Between 1.6 µm and 1.8 µm, the region labeled 176, hydrocarbons have strong absorption and show many spectral dependent features that must be detected. However, due to the limited number of channels of an FA spectrometer, it is not possible to capture all the spectral details. The FA spectrometer covers from visible to IR range, this invention allows for a hybrid spectrometer architecture to add greater channel density in specific spectral regions.

Figure 5:
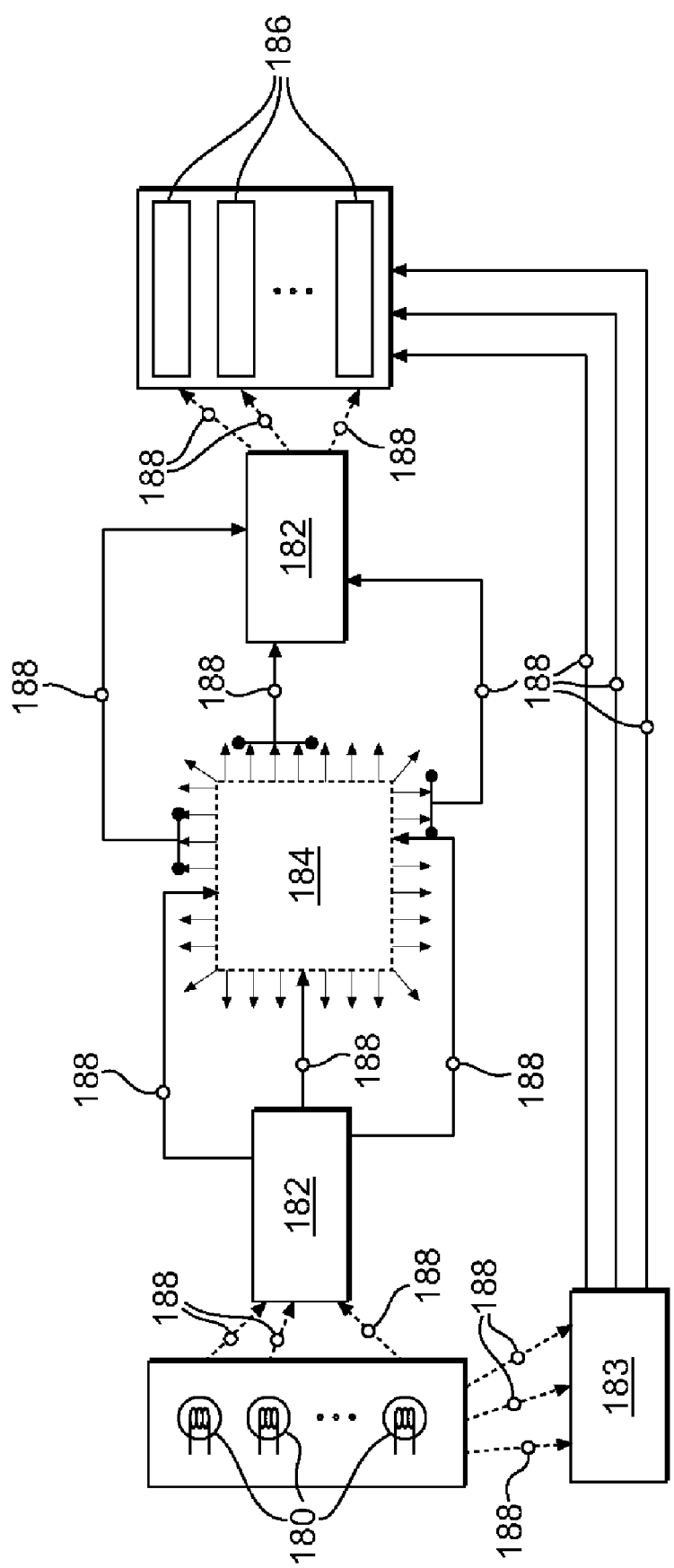
FIG. 5 is a schematic representation of one exemplary structure of a method and apparatus according to the present invention where light from multiple sources is routed to a plurality of spectrometers.

Turning now to FIG. 5, in the instant invention, two or more spectrometers are introduced downhole. In one embodiment of the present invention, at least one of the spectrometers may be an FA spectrometer and at least one may be a grating spectrometer. For example, the grating spectrometer may be configured to provide very high channel density in a limited range of wavelengths. It is useful in measuring spectral details in the important 1.6-1.8 µm range labeled 176. For example, the grating spectrometer may be configured to provide approximately 16 channels; these channels are in addition to the 10-20 channels provided by the FA spectrometer and provide more specific information about a smaller spectral range. For example, the FA spectrometer may be configured to measure in the visible and infrared range to determine the presence of fluids, such as water which has a peak at 1450 nm, and for baseline corrections, while the grating spectrometer may be configured to monitor the hydrocarbon range mentioned above. Other combinations of spectrometers are contemplated by the present invention such that a wide range of wavelengths are available for spectral analysis of downhole fluids. Spectral features in the visible range are limited, so the high channel density of the grating spectrometer is not as much of a necessity.

A schematic of one embodiment of the invention is shown in FIG. 5. Input light is provided by light source 180. As shown, there may be a plurality of different types of light produced at the light source. These include, but are not limited to, a halogen bulb (broad band light source), a light emitting diode (LED), and a laser. This input light may be processed by one of the light processing units 188. These light processing units may include any unit for changing a property of light, such as polarizer, amplitude and frequency modulators, among other light processing units. In one embodiment, the light then may be introduced to light collector 182 although this element is optional depending on the number of light sources and spectrometers in operation. This light collector is configured to allow light of different wavelengths to be routed to different locations or at different times. This is useful when it is desired to determine the affects of different light types independently. The input light then proceeds to one or more input windows of sample cell 184. This sample cell houses fluid flowing through the flowline which is the sample fluid to be tested. The light flows through the fluid and undergoes interactive change depending on the wavelength of the light and the composition of the fluid to produce an output light. For example, the input light may undergo reflection and/or absorption and/or light may be emitted as a result of interaction between the input light and the sample in the flowline. In this, the present invention contemplates a variety of known methodology for spectral analysis of fluids.

The output light traverses through an output window of the sample cell 184 and on to an optional light collector and router 182. The light is then routed to one of a plurality of spectrometers 186. As mentioned above, in one embodiment of the present invention, at least one of these may be an FA spectrometer and at least one of these may be a grating spectrometer. The output of these spectrometers, as mentioned above, will show the amounts of sample cell output light in a set of wavelength ranges.

In addition to the light incident on the sample cell, it is also advantageous to route light directly from the one or more light sources 180 to the plurality of spectrometers 186. The light sources, photodetectors, and processing electronics employed in conventional fluid analysis modules are typically adversely affected by the extreme temperatures and vibrations experienced downhole. For example, the optical power of light sources tends to diminish or drift when operated at elevated temperatures. Similarly, the optical gains of many photodetectors may drift by significant amounts when subjected to these high operating temperatures. These shifts may result in improper results, but calibration can be accomplished while testing to compensate for this drift. This calibration is accomplished by continuously directing light from the light sources 180 to the spectrometers 186. To accomplish this, light from the one or more light sources 180 is routed, via a fiber optic bundle, through optional light collector 183 and then on to the plurality of spectrometers 186. This light signal is referred to as the reference light signal, the light directed through sample cell 184 is referred to as the measurement light signal.

For calibration to be successful, it is necessary for the reference light signal and the measurement light signal to be separated before or at the plurality of spectrometers. This is because the spectrometers will detect all incident light, so for the signals to be compared, there must be some difference. In one embodiment, this differentiation may be performed by light processing units 188. These may include frequency modulators such as an optical chopper wheel. A chopper wheel is a disc that includes a set of openings that the light signal is directed toward. Based on the size of the openings, the light is transmitted at a certain frequency. The reference signal and the measurement signal are transmitted as different signals that can be determined so which signal is being measured by the spectrometers is known. The reference signal is then used in calibration while the measurement signal is used to determine the composition of fluid in the sample cell 184. Co-pending U.S. patent application Ser. No. 11/273,893 (incorporated herein by reference in its entirety) discloses real-time calibration for a downhole spectrometer.

Figure 6:
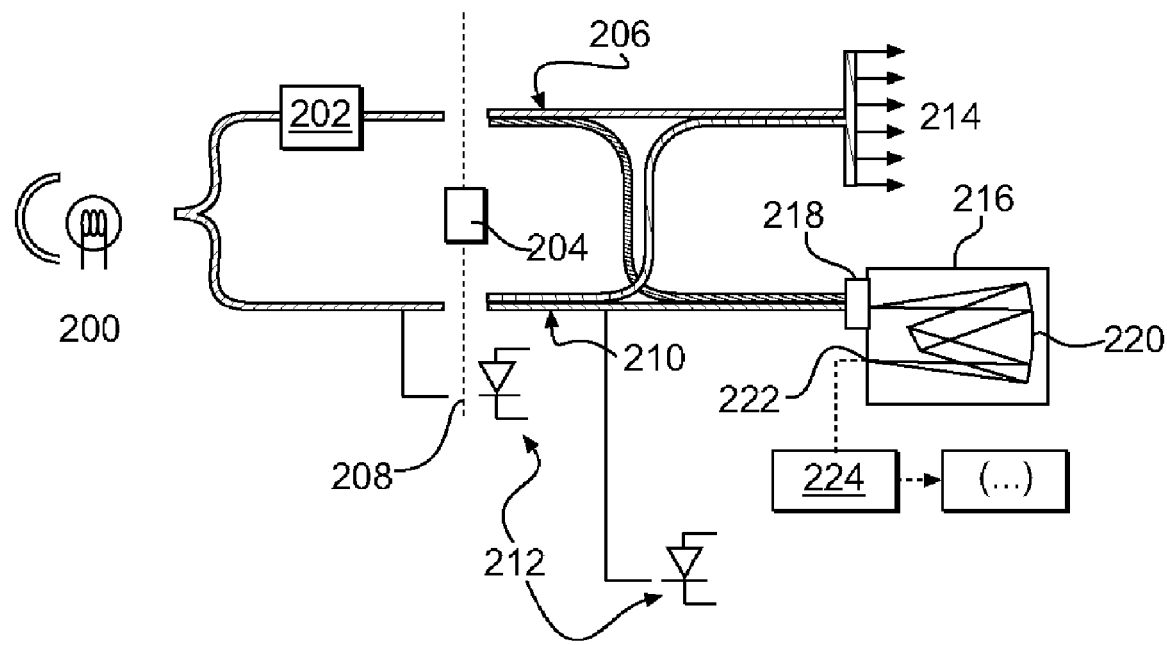
FIG. 6 is a schematic representation of one embodiment of a spectral analysis system according to the present invention.

FIG. 6 is a schematic representation of one spectral analysis system according to the present invention. Light is introduced by input light 200. Again, this may be a plurality of light sources depending on the application. The light is then split into two paths. The first is the measurement path and the light traverses through sample cell 202. This sample cell houses the downhole fluid that is to be analyzed. The second path is the reference path. Both paths then intersect with the rotating chopper wheel 208 at different points on the wheel. This wheel may be rotated by motor mechanism 204. This causes the frequency of each of the light signals to be modulated independently. The measurement light signal at point 206 has a first frequency and is split into two paths.

The reference light signal at point 210 has a second frequency and is split into two paths. These light signals are then routed to the spectrometers. The first spectrometer 214 may be an FA spectrometer as described above. The second spectrometer 216 may be a grating spectrometer. The light signals first pass through spectrometer input 218. This input also functions as a long pass filter for the light signals. Once inside grating spectrometer 216, the light is reflected off mirror 220 and eventually to the output of the grating spectrometer. A photodetector 222 is positioned at the output of the grating spectrometer to measure the light output and convert it to a current proportional to the amount of output light. This current is then converted to a voltage by I/V converter 224 and then passed on for further analysis. Photodiodes 212 are used in the synchronization of the signal before and after the chopper wheel.

Figure 7:
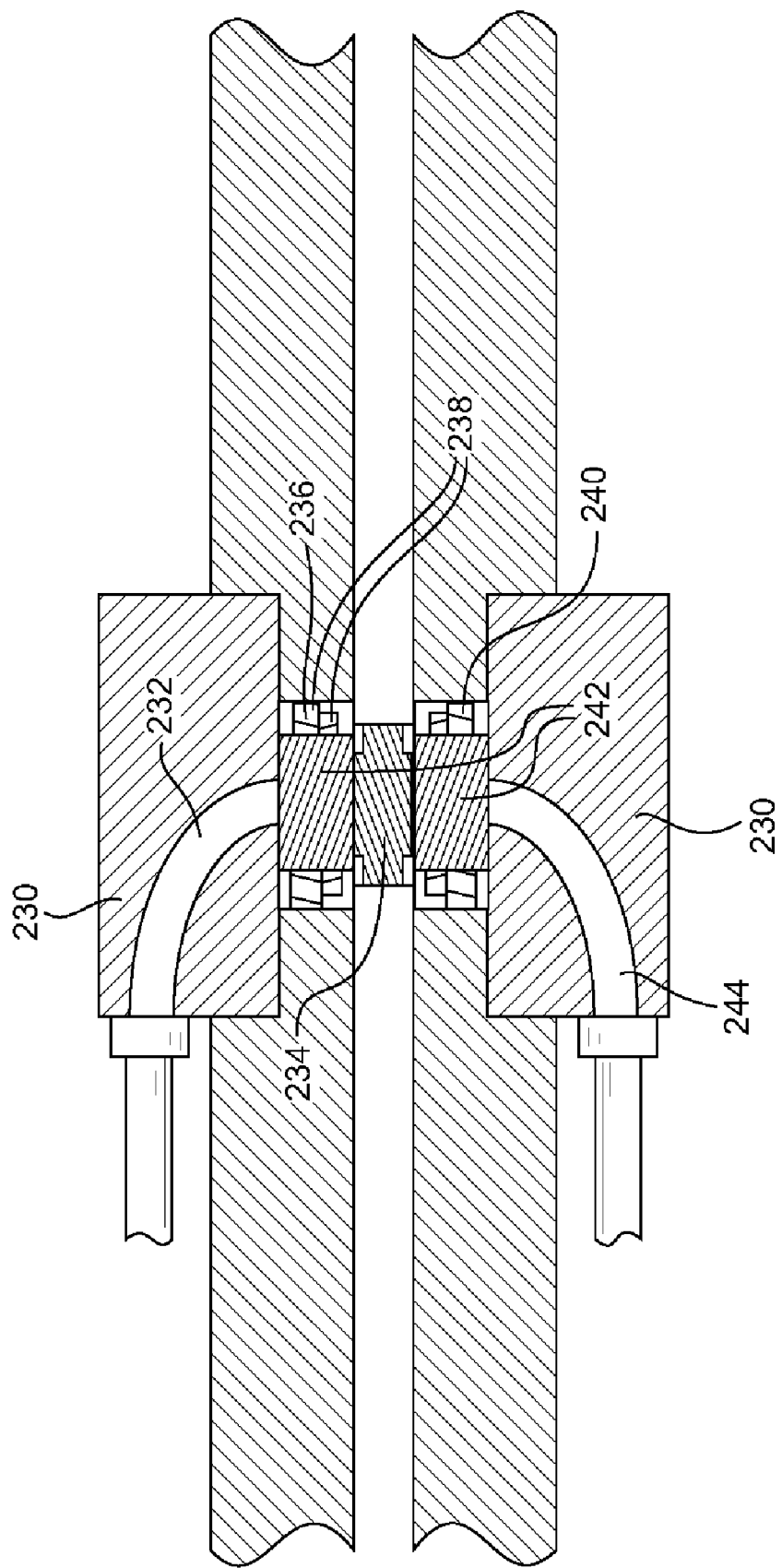
FIG. 7 is a cross-sectional schematic of an exemplary sample cell in one downhole implementation of a spectral analysis system according to the present invention.

FIG. 7 is a cross sectional view of one embodiment of a sample cell such as described in the previous figures. The depicted embodiment of the invention may be implemented in a plurality of other configurations. The sample fluid flows through flow channel 234. Opposed openings 236 and 240 are provided in the flowline each of which interfaces with an input or an output window and flange assemblies, respectively. Structurally, the input and output sides of the cell are identical, so only the input side will be described in detail. Flow channel 234 is located between openings 236 and 240 and defines window locating seats. Windows 242 are located on each side of the flow channel 234. In one embodiment, the windows may be made of sapphire. The windows 242 are secured in place by flanges 230 which are provided with optical connectors to connect the outer faces of the windows 242 with fiber bundles 232 and 244. The flanges may be screwed to each other so as to seal the windows into the seats. Sealing is assisted by the use of back up rings and O-rings 238. Inner and outer faces of the windows 242 are polished to optical quality, side faces are polished to assist in sealing.

FIG. 7 depicts just one sample cell with a single set of windows. There may be additional windows and fiber bundles that direct different types of light to different locations all traversing through the sample fluid. The light input through fiber bundle 232 interacts with the sample fluid and the output light is collected by fiber bundle 244. This received light signal is then forwarded on to the plurality of spectrometers for analysis.

Figure 8:
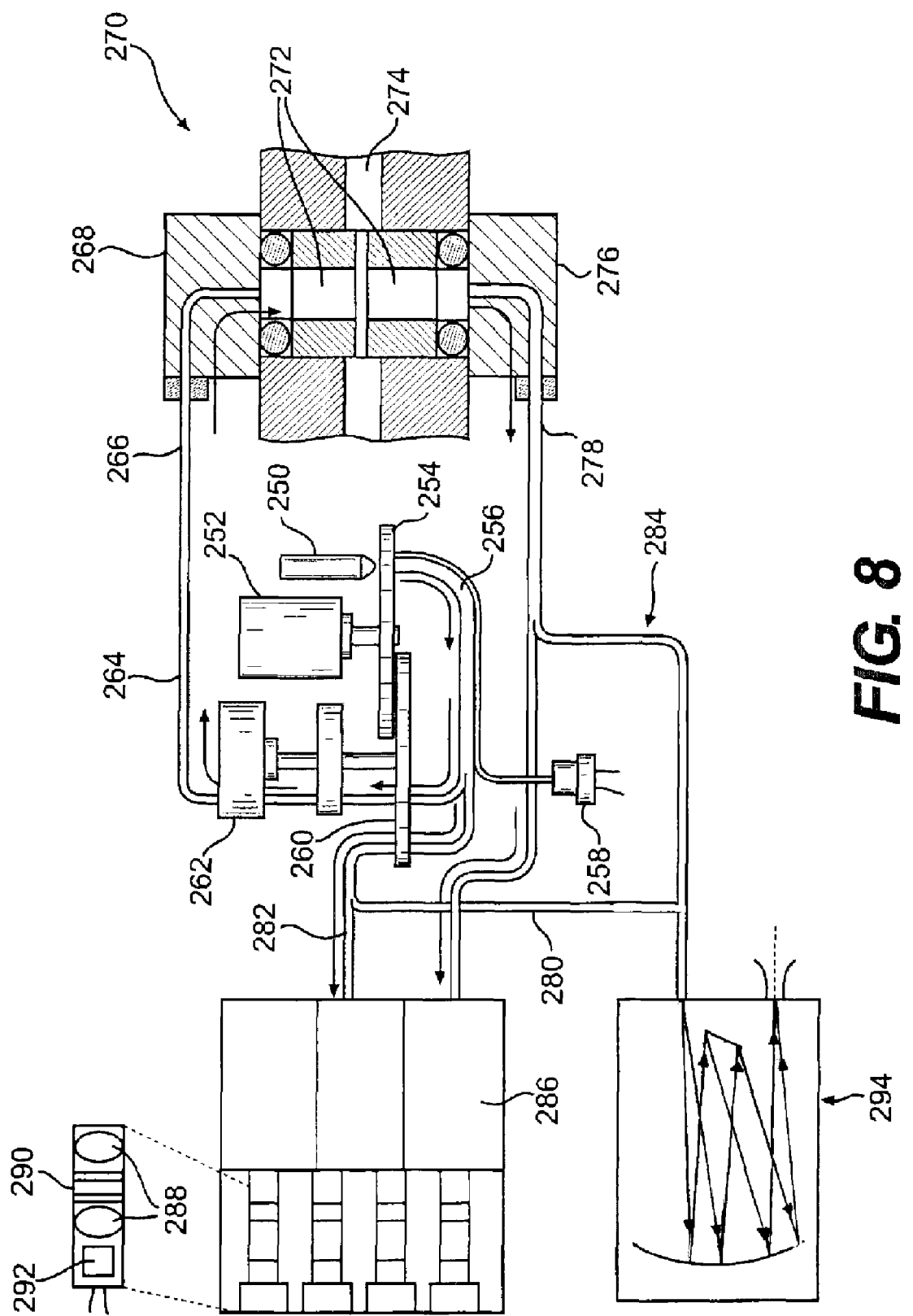
FIG. 8 is a schematic of another embodiment of a spectral analysis system according to the present invention.

FIG. 8 is a schematic representation of one embodiment of an overall structure for a spectral analysis system according to the present invention. Light source 250 passes light through a chopper wheel 254 driven by a chopper motor 252 into an optical fiber bundle 256. Outputs are taken from bundle 256 to provide input to a motor synchronization photodiode 258, a source light input path 282, a light distributor 286 (forming part of the detector described in more detail below) and to a measure path 264 which provides input to the spectrometer cell 270. A calibration wheel 260 driven by a rotary solenoid switch 262 selects whether light passes into the source light input path 282, the measure path 264, or both. The input fiber bundle 266 connects to the input flange 268 of the cell and optically connects to the window 272. Light is transmitted from the window 272, across the flow path 274 through another window 272 and into an output fiber bundle 278 connected to the output flange 276. The output bundle also connects to the light distributor 286. The light distributor 286 distributes the light received from the source light input 250 and the output fiber bundle 278 to a plurality of different channels.

For the purpose of this example, only four channels are shown but up to twenty may be available. This is a FA spectrometer described above that provides information on the output wavelengths from the sample fluid. Each channel comprises lens 288 and bandpass filter 290 feeding to a photodiode 292. The filters may be chosen to select predetermined wavelengths of light and provide an output signal relative to the wavelength in question. In addition to the FA spectrometer, a grating spectrometer 294 may also be provided. Path 280 is routed to the grating spectrometer 294. Path 280 is the reference signal that is provided directly from the light source to the spectrometer to be used in calibration. Path 284 is split from the output signal after the input light has been passed through the fluid sample. The light signal carried in path 284 is the measurement light signal and it is introduced to grating spectrometer 294.

The output of both spectrometers is then used in analysis of the fluid sample. The electrical outputs of the spectrometers are proportional to the light of a given wavelength range that is incident on the spectrometers. This invention provides a large number of channels covering a wide range of wavelengths all of which can be accomplished downhole in either a wireline or logging-while-drilling (LWD) or measurement-while-drilling (MWD) or production logging or permanent monitoring of a well type tools. Moreover, the present invention contemplates applicability in areas such as carbon-di-oxide sequestration and water reservoir management. In this, it is contemplated that the systems and methods disclosed herein will have wide ranging applications in a variety of downhole fluid analysis operations that employ conventional spectral analysis systems for downhole applications.

In the systems and methods disclosed herein, light from one or more light sources 180 is directed at a sample cell 184 to interact with a sample fluid therein, and output light is collected in fiber bundles and routed to two or more spectrometers 186. For example, a filter array spectrometer may be configured to provide information over a wide spectral range, a grating spectrometer may be configured for a finer analysis of a smaller range of wavelengths that are of special interest in determining the presence of desired hydrocarbons.

In addition to one function of measurements of light received from a sample fluid, light may also be routed directly from the light sources to the two or more spectrometers. This reference signal is used in calibration of the spectrometers and associated electronics as their performance may change in the high temperature and noise environment downhole.

The preceding description has been presented only to illustrate and describe the invention and some examples of its implementation. It is not intended to be exhaustive or to limit the invention to any precise form disclosed. Many modifications and variations are possible in light of the above teaching.

The preferred aspects were chosen and described in order to best explain principles of the invention and its practical applications. The preceding description is intended to enable others skilled in the art to best utilize the invention in various embodiments and aspects and with various modifications as are suited to the particular use contemplated. It is intended that the scope of the invention be defined by the following claims.

What is claimed is:

1. A fluid analysis system configured to operate downhole in a well traversing a formation comprising:

at least one light source generating an input light across a wide, continuous spectral range;

a sample cell operable to receive a flowing sample fluid therein, said sample cell further comprising:

at least one input window allowing said input light to flow into said sample cell and through the flowing sample fluid to produce an output light;

at least one output window allowing said output light to flow out of said sample cell;

two or more downhole spectrometers configured to measure said output light and generate a plurality of measurement signals; and an analysis device configured to receive said plurality of measurement signals and determine properties of the flowing sample fluid.

2. The fluid analysis system configured to operate downhole as defined in claim 1 further comprising:

a plurality of light sources wherein said plurality of light sources generate light across a wide spectral range.

3. The fluid analysis system configured to operate downhole as defined in claim 1, wherein one of said two or more spectrometers comprises a filter array spectrometer.

4. The fluid analysis system configured to operate downhole as defined in claim 1, wherein one of said two or more spectrometers comprises a grating spectrometer.

5. The fluid analysis system configured to operate downhole as defined in claim 1, wherein said two or more spectrometers comprise at least one filter array spectrometer and at least one grating spectrometer.

6. The fluid analysis system configured to operate downhole as defined in claim 1, wherein said at least one light source comprises a halogen lamp.

7. The fluid analysis system configured to operate downhole as defined in claim 1, wherein said at least one light source comprises a light emitting diode (LED).

8. The fluid analysis system configured to operate downhole as defined in claim 1, wherein said at least one light source comprises a laser.

9. The fluid analysis system configured to operate downhole as defined in claim 1 further comprising:

a plurality of light processing units for processing said input light and said output light.

10. The fluid analysis system configured to operate downhole as defined in claim 1 further comprising at least one of:

a first light collector positioned between said at least one light source and said sample cell; and a second light collector positioned between said sample cell and said two or more spectrometers.

11. The fluid analysis system configured to operate downhole as defined in claim 10, wherein said first and second light collectors further comprise a router configured to selectively route light to at least one of a specific input window, a specific spectrometer, and at a specific time.

12. The fluid analysis system configured to operate downhole as defined in claim 9, wherein said plurality of processing units comprises at least one amplitude modulator.

13. The fluid analysis system configured to operate downhole as defined in claim 9, wherein said plurality of processing units comprises at least one frequency modulator.

14. A fluid analysis system configured to operate downhole in a well traversing a formation comprising:

at least one light source generating an input light across a wide, continuous spectral range;

a sample cell operable to receive a sample fluid therein, said sample cell further comprising:

at least one input window allowing said input light to flow into said sample cell and through the sample fluid to produce an output light;

at least one output window allowing said output light to flow out of said sample cell;

two or more downhole spectrometers configured to measure said output light and generate a plurality of measurement signals;

an analysis device configured to receive said plurality of measurement signals and determine properties of the sample fluid; and a reference light collector positioned between said at least one light source and said two or more spectrometers, said reference light collector operable to route said input light directly from said at least one light source to said two or more spectrometers for a reference measurement.

15. The fluid analysis system configured to operate downhole as defined in claim 14 further comprising:

one or more light processing units between said reference light collector and said two or more spectrometers.

16. A method for downhole fluid analysis comprising:

providing input light using at least one light source generating an input across a wide, continuous spectral range;

inserting a flowing sample fluid into a sample cell;

introducing said input light to an input window of said sample cell, said light traversing through said flowing sample fluid and producing an output light traversing through an output window in said sample cell;

receiving said output light at two or more downhole spectrometers;

generating a plurality of measurement signals by said two or more spectrometers based on said output light; and analyzing said plurality of measurement signals to determine properties of said flowing sample fluid.

17. The method for downhole fluid analysis defined in claim 16 further comprising:

providing input light from a plurality of light sources wherein said plurality of light sources generate light across a wide spectral range.

18. The method for downhole fluid analysis defined in claim 16 further comprising:

processing said input light before introduction to said sample cell.

19. The method for downhole fluid analysis defined in claim 18, wherein said processing comprises modulating the amplitude of said input light.

20. The method for downhole fluid analysis defined in claim 18, wherein said processing comprises modulating the frequency of said input light.

21. A method for downhole fluid analysis comprising:

providing input light using at least one light source generating an input light across a wide, continuous spectral range;

inserting a sample fluid into a sample cell;

introducing said input light to an input window of said sample cell, said light traversing through said sample fluid and producing an output light traversing through an output window in said sample cell;

receiving said output light at two or more downhole spectrometers;

generating a plurality of measurement signals by said two or more spectrometers based on said output light; and analyzing said plurality of measurement signals to determine properties of said sample fluid;

introducing said input light directly to said two or more spectrometers;

generating a plurality of reference signals from said two or more spectrometers;

calibrating said spectrometers using said plurality of reference signals.

* * * * *